United States Patent [19]
Campbell et al.

[11] Patent Number: 5,783,723
[45] Date of Patent: Jul. 21, 1998

[54] PROCESS FOR THE PREPARATION OF DIALKYL SUCCINYLSUCCINATES

[75] Inventors: Colin Dennis Campbell, Claymont, Del.; Damien Thurber Cole, Upper Darby, Pa.; Harold Raymond Taylor, III, Wilmington, Del.

[73] Assignee: Ciba Specialty Chemicals Corporation, Tarrytown, N.Y.

[21] Appl. No.: 719,044

[22] Filed: Sep. 24, 1996

Related U.S. Application Data

[60] Provisional application No. 60/004,237, Sep. 25, 1995 and provisional application No. 60/022,339, Jul. 24, 1996.

[51] Int. Cl.$^6$ .................. C07C 229/00; C07C 69/74; C07D 221/18
[52] U.S. Cl. .................. 560/48; 546/58; 560/126
[58] Field of Search .................. 560/48, 126; 546/58

[56] References Cited

U.S. PATENT DOCUMENTS

| | | | |
|---|---|---|---|
| 3,124,581 | 3/1964 | Bohler et al. | 560/48 X |
| 4,435,589 | 3/1984 | Rolf et al. | 560/48 |
| 5,208,365 | 5/1993 | Fuchs et al. | 560/48 |
| 5,347,038 | 9/1994 | Arndt et al. | 560/48 |
| 5,367,096 | 11/1994 | Ritter et al. | 560/48 |

FOREIGN PATENT DOCUMENTS

| | | | |
|---|---|---|---|
| 0166214 | 2/1988 | European Pat. Off. | 560/48 |

OTHER PUBLICATIONS

Mielsen et al. Organic Synthesis, 45, 25–31 (1973).
Mussee et al. Ber, 97, 1147 (1964).
Georha, et al. Jour. Indian Chem. Soc. vol. 41, No. 8 (1964).
Organic Reactions I, 283–289 (1942).
Piutti, Gay, Chim. Ital., 20, 165–178 (1890) Partial translation of p. 167.
H. Ebert, Ann, vol. 229, 52 (1885).
JeaneNaud, Ber., 22, 1982 (1889).
Liebermann, Ann, 404, 272–321 (1914).
Vincent et al. J. Org. Chem., 3, 603 (1938).
Derwent Abstracts, 87–027586, (Dec. 16, 1986–JP 61 286 343).

*Primary Examiner*—Floyd D. Higel
*Attorney, Agent, or Firm*—Kevin T. Mansfield; George R. Dohmann

[57] ABSTRACT

Dialkyl succinylsuccinates are prepared in a pure form and in high yield by reacting an alkali metal alcoholate with an excess of dialkyl succinate under anhydrous conditions followed by isolation of the di(alkali metal) salt of the dialkyl succinylsuccinate and then neutralization of the salt with acid. The resulting dialkyl succinylsuccinate is isolated or used without isolation as an intermediate in the production of quinacridone pigments. The disclosed process provides for high yields and reduced organic waste compared with known processes.

25 Claims, No Drawings

PROCESS FOR THE PREPARATION OF DIALKYL SUCCINYLSUCCINATES

This application claims the benefit under 35 U.S.C. 119(e) of U.S. Provisional Application No. 60/004,237, filed Sep. 25, 1995 and U.S. Provisional Application No. 60/022,339 filed Jul. 24, 1996.

SUMMARY

Dialkyl succinylsuccinates are prepared in a pure form and in high yield by the reaction of an alkali metal alcoholate with an excess of dialkyl succinate under anhydrous conditions, isolating the solid di(alkali metal) salt of the dialkyl succinylsuccinate under anhydrous conditions and then neutralizing the salt with acid to yield the free dialkyl succinylsuccinate. The use of anhydrous conditions during the reaction and isolation permits the excess dialkyl succinate to be easily regenerated for reuse in a subsequent reaction.

BACKGROUND

It is known in the art to prepare dialkyl succinylsuccinates, which are also known as dialkyl 2,5-dihydroxy-3,6-dihydroterephthalates or dialkyl cyclohexane-1,4-dione-2,5-dicarboxylates, by the reaction of a dialkyl succinate with an alkali metal or an alkali metal alcoholate in the presence or absence of one or more co-solvents or diluents, one of which is usually an alcohol. It is preferred to use an alkali metal alcoholate due to the fire and explosion hazards associated with handling alkali metals.

Most known processes which utilize an alkali metal alcoholate react the dialkyl succinate with greater than the theoretical amount of the alkali metal alcoholate. For example, U.S. Pat. No. 4,435,589 discloses a process wherein dimethyl succinate is added to a methanolic solution containing 120 to 180 percent of the theoretical weight of sodium methylate to produce dimethyl succinylsuccinate disodium salt and dimethyl succinylsuccinate by subsequent acidification.

It is also known to utilize an excess of the dialkyl succinate reagent. For example, EP 166,214 discloses a process wherein a 5 to 45% solution of alkali metal alcoholate in alcohol is added to an excess of the dialkyl succinate. After distilling the alcohol, the dialkyl succinylsuccinate alkali metal salt is neutralized, without isolation, to yield the dialkyl succinylsuccinate by mixing an aqueous acid with the mixture containing the excess dialkyl succinate and dialkyl succinylsuccinate alkali metal salt. The disclosure provides that the excess dialkyl succinate can be recovered and reused. However, since the excess dialkyl succinate is combined with the aqueous acid prior to recovery, it is necessary to separate the aqueous and organic phases. Losses in yield can occur due to the solubility of dialkyl succinylsuccinate in dialkyl succinate and in the recovery of dialkyl succinate from aqueous acidic media.

The present invention relates to a novel process for the preparation of a high purity dialkyl succinylsuccinate in high yield. The high yield is based on both the dialkyl succinate and the alkali metal alcoholate. According to the inventive process an alkali metal alcoholate is reacted with an excess of the dialkyl succinate reagent in the presence of an aliphatic alcohol under anhydrous conditions, the initially formed non-crystalline complex between dialkyl succinylsuccinate di(alkali metal) salt and dialkyl succinate is transformed into a crystalline dialkyl succinylsuccinate di(alkali metal) salt and the dialkyl succinylsuccinate is isolated and washed as its di-alkali metal salt prior to a neutralization step. The use of anhydrous reaction conditions and isolation of the di(alkali metal) salt of the dialkyl succinylsuccinate from organic media permits the ready separation, recovery and reuse of an economically significant portion of the excess dialkyl succinate reagent and the aliphatic alcohol. The aliphatic alcohol is used as a solvent and generated as a reaction product.

DETAILED DESCRIPTION

The present invention relates to the preparation of a dialkyl succinylsuccinate by a process which comprises the steps of: (a) preparing a dialkyl succinylsuccinate di(alkali metal) salt by reacting a mixture consisting essentially of an alkali metal alcoholate, an aliphatic alcohol and an excess of a liquid dialkyl succinate under anhydrous conditions at an elevated temperature; (b) removing the aliphatic alcohol from the reaction mixture; (c) separating the solid dialkyl succinylsuccinate di(alkali metal) salt from an anhydrous supernatant liquid; and (d) neutralizing the dialkyl succinylsuccinate di(alkali metal) salt to yield the dialkyl succinylsuccinate.

The reaction of a dialkyl succinate with a sodium alcoholate to yield a dialkyl succinylsuccinate di(alkali metal) salt according to the present process is described by the following chemical equations:

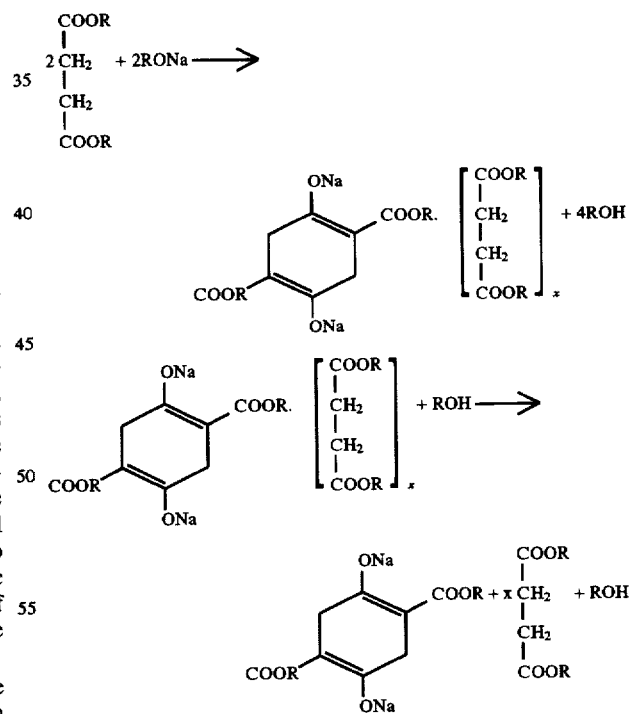

wherein each R is an alkyl group, preferably a $C_1$–$C_6$ alkyl group, most preferably a $C_1$–$C_3$ alkyl group, and x is a numeric value which is $>0$ and $\leq 1$. It is preferable for all of the R groups to be the same.

The neutralization step is described by the following chemical equation:

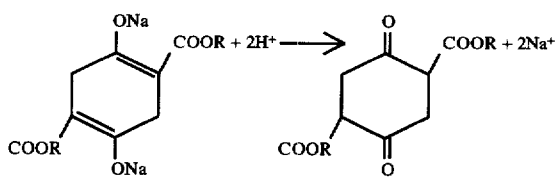

The inventive process provides for improved yields based on unrecoverable dialkyl succinate compared with known processes. For example, the present process generally yields 85 percent by weight or greater of the dialkyl succinylsuccinate based on unrecoverable dialkyl succinate. Unrecoverable dialkyl succinate is the amount charged minus the amount recoverable from all sources. Unrecoverable dialkyl succinate includes the dialkyl succinate that is converted to dialkyl succinylsuccinate and the dialkyl succinate that cannot be accounted for at the end of the process, being converted to by-products or lost in material processing. In general, the excess dialkyl succinate is recoverable from the alcoholic distillate of step (b) and the isolation step (c) of the process. The liquid mixtures from these steps can be combined and the dialkyl succinate and the aliphatic alcohol separated for reuse, for example, by fractional distillation.

Since there is an excess of the dialkyl succinate, virtually all of the alkali metal alcoholate reacts during the course of the reaction. Due to the small amount of by-products produced, yields are also at least 85 percent of theory based on the alkali metal alcoholate.

The following is an example of a typical yield calculation when dimethyl succinate (molecular weight=146) and sodium methylate (molecular weight=54) are converted to dimethyl succinylsuccinate (molecular weight=228) in the presence of methanol:

groups may be different from each other, but are preferably the same. Most preferably, the dialkyl succinate is dimethyl succinate or diethyl succinate.

The dialkyl succinate is combined with an alkali metal alcoholate and an aliphatic alcohol under anhydrous conditions according to the present process. In general, the reaction is best run at an elevated temperature, for example, from 60° to 140° C., preferably 90° to 110° C. In general, it is advantageous to apply a slight vacuum to the system to assist in the removal of the aliphatic alcohol, which is generated by the reaction, from the reaction mixture. Thus a vacuum of 100 to 500 mm Hg may be applied to remove the aliphatic alcohol.

Alkali metal alcoholates are known in the art and are generally prepared by reacting an alkali metal with an alcohol. The present process can be carried out using an alkali metal which is added to the dialkyl succinate containing a small quantity of aliphatic alcohol under anhydrous, inert conditions. The alkali metal alcoholate is formed in situ and reacts with the dialkyl succinate as already described. Since the reaction generates four parts of aliphatic alcohol for every one part of dialkyl succinylsuccinate di(alkali metal) salt formed, no further addition of aliphatic alcohol is necessary when alkali metal is used to generate the alkali metal alcoholate in situ. The generation of the alkali metal alcoholate in situ thus has the advantage of using less aliphatic alcohol. The alkali metal may be added as a solid but is preferably added in its molten form.

In general, however, alkali metal alcoholates of aliphatic alcohols are preferred, for example, an alkali metal $C_1$–$C_6$ alkyl alcoholate, or preferably, an alkali metal $C_1$–$C_3$ alkyl alcoholate. Preferably, the alkali metal is sodium or potassium. Sodium methylate and sodium ethylate are preferred alkali metal alcoholates. In general, commercially available alkali metal alcoholates as dry powder, or as anhydrous

| | |
|---|---|
| Parts by weight of dimethyl succinate (at 100% purity) charged = | A |
| Parts by weight of sodium methylate (at 100% purity) charged = | B |
| Parts by weight of dimethyl succinylsuccinate (at 100% purity) obtained = | y |
| Parts by weight of recoverable dimethyl succinate from all sources = | z |
| Parts by weight of unrecoverable dimethyl succinate = | A − z |
| Theoretical yield based on sodium methylate = | (228/108) × B |
| Theoretical yield based on dimethyl succinate = | (228/292) × (A − z) |
| Percent yield of dimethyl succinylsuccinate = | $\frac{\text{actual yield (y)}}{\text{theoretical yield}} \times 100$ |

The environmental advantages of the present process are clearly seen by the high yields of product (dialkyl succinylsuccinate) and the ready recovery of the excess dialkyl succinate. Since the anhydrous aliphatic alcohol is generally recovered from the distillate obtained according to step (b) and from separation step (c), the anhydrous dialkyl succinate is generally recoverable from steps (b) and (c), organic waste material generated by the inventive process generally consists of only (i) residue remaining after the dialkyl succinate and any washing solvents are recovered from the isolation step (c), and (ii) a small quantity of unrecoverable solvent leaving the neutralization process with the aqueous acid if the dialkyl succinylsuccinate di(alkali metal) salt is neutralized as a solvent slurry rather than as a dry powder.

Dialkyl succinylsuccinates are well-known in the art as intermediates for the production of quinacridone pigments. Preferably, the alkyl groups in the dialkyl succinate are two straight or branched alkyl groups, for example two $C_1$–$C_6$ alkyl groups. Preferably, the dialkyl succinate has two $C_1$–$C_3$ alkyl groups as the dialkyl substituents. The alkyl solutions in aliphatic alcohols, are suitable for use in the current process.

Any anhydrous aliphatic alcohol is suitable for use in step (a). Preferably, the aliphatic alcohol is a $C_1$–$C_6$ aliphatic alcohol. Most preferably, the aliphatic alcohol is a $C_1$–$C_3$ aliphatic alcohol, such as methanol, ethanol and 1- or 2-propanol.

In general, commercially available anhydrous aliphatic alcohols are sufficiently anhydrous for use as the aliphatic alcohol in the present process.

In general, the alkali metal alcoholate is added to the reaction mixture as a 10 to 50 percent by weight anhydrous solution of the alkali metal alcoholate in the aliphatic alcohol. Most preferably, the anhydrous solution is a 25 to 35 percent by weight solution of the alkali metal alcoholate in the aliphatic alcohol. Preferably, the anhydrous solution consists of only the alkali metal alcoholate and the aliphatic alcohol.

In general, from 0.1 to 0.5 moles, preferably 0.2 to 0.4 moles, of the alkali metal alcoholate are added to the reaction mixture per mole of liquid dialkyl succinate.

It is generally preferred for the alkali metal alcoholate to be derived from the same aliphatic alcohol that is used to dissolve it, for example, an anhydrous solution of sodium methylate in methanol or sodium ethylate in ethanol.

Most preferably, the dialkyl succinate, the alkali metal alcoholate and the aliphatic alcohol have alkyl groups that are identical. This avoids the need for separating the alcohols during recovery processes. For example, a process wherein the dialkyl succinate is dimethyl succinate, the alkali metal alcoholate is sodium methylate and the aliphatic alcohol is methanol, or the dialkyl succinate is diethyl succinate, the alkali metal alcoholate is sodium ethylate and the aliphatic alcohol is ethanol.

In step (b) the aliphatic alcohol is removed from the reaction mixture by any means known in the art. Preferably, the aliphatic alcohol is removed from the reaction mixture by distillation at atmospheric pressure or by distillation under reduced pressure, for example at a reduced pressure of from 100 to 500 mm of Hg, preferably in the range from 250 to 500 mm of Hg. Step (b) is preferably carried out concurrently with step (a).

In order to obtain high yields, it is necessary to remove a significant portion of the aliphatic alcohol, which is produced by the reaction and/or added to the reaction mixture, from the reaction mixture to permit the temperature to be at a level which promotes the reaction. Generally, sufficient aliphatic alcohol is removed to keep the reaction mixture at a temperature above about 80° C., preferably in the range from 90° to 110° C..

Removal of the aliphatic alcohol from the reaction mixture initially yields a dialkyl succinylsuccinate di(alkali metal) salt which is a complex formed with dialkyl succinate. The complex is subsequently converted to non-complexed dialkyl succinylsuccinate di(alkali metal) salt.

In addition to increasing yield by removing a reaction product, the removal of the aliphatic alcohol serves as an indicator for the completion of the reaction because production of the aliphatic alcohol stops when the reaction is complete.

Improved yields are obtained when the mixture of the precipitated complex of dialkyl succinylsuccinate di(alkali metal) salt and dialkyl succinate in liquid dialkyl succinate, in the presence of a small amount of the aliphatic alcohol, is maintained at an elevated temperature, preferably about the elevated temperature of step (a), for example above 80° C., preferably in the range from 90° to 110° C., for a period greater than about 30 minutes, for example for from 45 minutes to 2 hours, prior to converting the complexed dialkyl succinylsuccinate di(alkali metal) salt to non-complexed dialkyl succinylsuccinate di(alkali metal) salt. During this period, the aliphatic alcohol is allowed to reflux at atmospheric pressure. At the end of this period, the yield is improved further if the remaining aliphatic alcohol is removed and combined with the other aliphatic alcohol fractions of step (b).

If desired, the complex between dialkyl succinylsuccinate di(alkali metal) salt and dialkyl succinate is isolated by filtration and purified by washing with hexane. In general, the complex is converted into its constituent parts without isolation in the reaction mixture.

The washed and dried dialkyl succinylsuccinate di(alkali metal) salt-dialkyl succinate complex is characterized by infared spectroscopy and readily distinguished from a physical mixture of dialkyl succinylsuccinate di(alkali metal) salt and dialkyl succinate. In the case of the alkyl groups being methyl and the alkali metal being sodium, wavelength shifts are recorded in the region 1000 to 2000 $cm^{-1}$ as follows:

| wavelength $cm^{-1}$ | |
|---|---|
| complex | physical mixture |
| 1742 | 1740 |
| 1654 | 1646 |
| 1520 | 1518 |
| 1434 | 1440 |
| 1386 | 1386 |
| 1326 | 1322 |
| 1244 | 1252 |
| 1182 | 1196 |
| 1162 | 1164 |
| 1074 | 1078 |
| 1004 | 1002 |

Generally, the complexed dialkyl succinylsuccinate di(alkali metal) salt is converted to the dialkyl succinylsuccinate di(alkali metal) salt by adding an second anhydrous aliphatic alcohol back into the reaction mixture, but is preferably carried out by transferring the reaction mixture into a second anhydrous aliphatic alcohol with agitation. The second anhydrous aliphatic alcohol can be different from, but is preferably the same as, the aliphatic alcohol of step (a). The amount of the second anhydrous aliphatic alcohol necessary to achieve good conversion of the complex into its component parts is about 3 to 10 times the weight of the alkali metal alcoholate, preferably 5 to 8 times. The temperature of the reaction mixture prior to the conversion is generally about 30° to 120° C., but is preferably 90°–110° C. The temperature of the aliphatic alcohol is initially about 15° to 30° C. and is generally about 30° to 50° C. after the addition of the reaction mixture. It is advantageous to keep the alcoholic slurry at a cool temperature (<about 30° C.) before step (c).

Generally, step (c) is carried out by any method used in the art for separating a solid from an anhydrous liquid. Step (c) is generally carried out by a filtration method, such as filtration by press, pressure nutsch or leaf filter, or by a centrifuge method. Since the reaction mixture is preferably combined with a second anhydrous aliphatic alcohol in step (b) to convert the complex to the dialkyl succinylsuccinate di(alkali metal) salt, the supernatant liquid in step (c) is generally an anhydrous mixture of the dialkyl succinate and an aliphatic alcohol.

Step (c) generally includes several washing steps wherein the solid dialkyl succinylsuccinate di(alkali metal) salt is washed with an anhydrous solvent to remove excess dialkyl succinate and solvent-soluble by-products. Preferably, the anhydrous solvent used for the washing does not react with or dissolve appreciable amounts of the salt. In general, commercially available anhydrous solvents are sufficiently anhydrous for use as the anhydrous washing solvent in the present process. Most preferably, the anhydrous solvent is readily separated from the dialkyl succinate that is washed off the solid salt, for example by distillation, at atmospheric or reduced pressure. Suitable solvents include anhydrous lower aliphatic alcohols, ketones, ethers and hydrocarbon solvents or aromatic ethers or hydrocarbons or mixtures of these solvents. In particular, the anhydrous solvent is an anhydrous $C_1$–$C_6$ aliphatic alcohol. Preferably, the aliphatic alcohol is a $C_1$–$C_3$ aliphatic alcohol, such as methanol, ethanol and 1- or 2-propanol. Most preferably, the anhydrous solvent is a $C_1$–$C_3$ aliphatic alcohol which is identical to the aliphatic alcohol used in step (a) and the second anhydrous aliphatic alcohol used for the conversion in step (b).

According to step (d), dialkyl succinylsuccinate di(alkali metal) salt is neutralized to yield the dialkyl succinylsuccinate, which can be isolated or used as a reactant for the production of quinacridones without isolation. Generally, the dialkyl succinylsuccinate di(alkali metal) salt is neutralized simply by mixing it with an acid, preferably an aqueous mineral acid, for example, hydrochloric acid, sulfuric acid, phosphoric acid or carbonic acid, or an aqueous organic acid, such as formic acid or acetic acid. Preferably, the aqueous mineral acid is a 10 to 20 percent by weight solution of a mineral acid in water, for example a 15 percent by weight solution of sulfuric acid in water. An amount of acid which converts all of the dialkyl succinylsuccinate di(alkali metal) salt to dialkyl succinylsuccinate and finishes with a pH of the aqueous mother liquor in the range from 1 to 7, preferably 3 to 6, is generally selected.

The washed dialkyl succinylsuccinate di(alkali metal) salt is neutralized in step (d) as a dry powder (obtained, for example, by drying with heated nitrogen), as a wet solid directly from the isolation device or as a pumpable slurry by reconstituting the dialkyl succinylsuccinate di(alkali metal) salt with fresh anhydrous solvent.

If the dialkyl succinylsuccinate is isolated, it is generally isolated by the methods described above for separating a solid from a liquid. Residual water-soluble salts from the neutralization process and water-soluble organic residues on the dialkyl succinylsuccinate are removed by appropriate washing, in general, with water, which may be artificially softened, de-ionized or distilled. The dialkyl succinylsuccinate may be dried (for example, in a vacuum paddle drier) or used in subsequent steps as a wet solid or a pumpable slurry.

From the discussion above, it is clear that preferred embodiments of the present process include additional process steps. For example, a preferred embodiment includes the following steps:

(a) producing a dialkyl succinylsuccinate di(alkali metal) salt by reacting a mixture consisting essentially of an alkali metal alcoholate, an aliphatic alcohol and an excess of a dialkyl succinate at elevated temperature under anhydrous conditions;

(b) removing a substantial portion of the aliphatic alcohol from the reaction mixture, subsequent to or concurrently with step (a);

(b1) maintaining the reaction mixture resulting from step (b) at an elevated temperature, such as the reflux temperature, for a period greater than 30 minutes;

(b2) optionally removing the remaining aliphatic alcohol;

(b3) combining the reaction mixture with a second aliphatic alcohol to yield non-complexed dialkyl succinylsuccinate di(alkali metal) salt in an anhydrous supernatant liquid;

(c) separating the dialkyl succinylsuccinate di(alkali metal) salt from the reaction mixture;

(d) neutralizing the dialkyl succinylsuccinate di(alkali metal) salt to yield a dialkyl succinylsuccinate; and (d1) optionally recovering the dialkyl succinate and/or aliphatic alcohol from steps (b) and (c) for reuse. In general, steps (b), (b1), (b2) and (b3) are carried out sequentially.

In a preferred embodiment of the present process, step (a) is carried out by adding an anhydrous solution of the alkali metal alcoholate in the aliphatic alcohol to the liquid dialkyl succinate. In general, from 0.1 to 0.5 moles, preferably 0.2 to 0.4 moles, of the alkali metal alcoholate are added per mole of liquid dialkyl succinate. Normally, the anhydrous solution is added to the liquid dialkyl succinate over an extended period of time, for example over from about 30 minutes to about 4 hours, for example at a rate of from 0.01 to 0.1 parts by weight of the alkali metal alcoholate per hour per part of the dialkyl succinate.

As the anhydrous solution is added to the liquid dialkyl succinate, the alcohol is removed by distillation, for example at reduced pressure. Thus, the present process embraces a process wherein the alcohol is removed from the reaction mixture by distillation at reduced pressure concurrently with adding the anhydrous solution to the dialkyl succinate.

The preferences discussed above also apply to the preferred embodiment. For example, it is preferable if the dialkyl succinate, the alkali metal alcoholate and the aliphatic alcohols have alkyl groups that are identical, for example if the dialkyl succinate is dimethyl succinate, the alkali metal alcoholate is sodium methylate and the aliphatic alcohols are methanol, or if the dialkyl succinate is diethyl succinate, the alkali metal alcoholate is sodium ethylate and the aliphatic alcohol is ethanol. It is also preferable if the alkali metal alcoholate is added as a 10 to 50 percent by weight solution of the alkali metal alcoholate in the alcohol. In addition, as described above, it is preferable to maintain the complex of solid dialkyl succinylsuccinate di(alkali metal) salt and dialkyl succinate in liquid dialkyl succinate at an elevated temperature for a period of from 45 minutes to 2 hours prior to step (c), for the anhydrous solvent used in washings to be a $C_1$–$C_3$ aliphatic alcohol, most preferably identical to the aliphatic alcohol of step (a), and for the dialkyl succinylsuccinate di(alkali metal) salt to be neutralized with aqueous sulfuric acid.

The present invention further relates to a novel complex of the formula

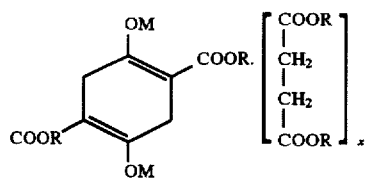

wherein M is an alkali metal, each R is independently $C_1$–$C_6$ alkyl, and x is a numeric value which is >0 and ≦1, preferably wherein M is sodium or potassium and each R is independently $C_1$–$C_3$ alkyl. The complex is an intermediate in the present process that can be isolated and purified, for example by filtration and washing with an inert solvent, prior to further processing, or separated into its constituent parts without isolation.

The dialkyl succinylsuccinate products of the present process are useful intermediates in the preparation of quinacridone pigments. Thus, the present invention further relates to a process for the preparation of a quinacridone compound of the formula

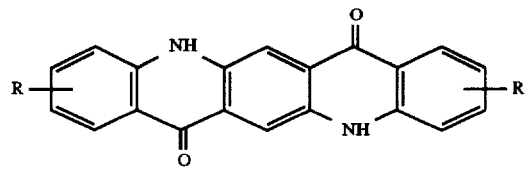

wherein each R is independently hydrogen, unsubstituted or substituted $C_1$–$C_6$ alkyl, preferably methyl, ethyl or trifluoromethyl, halogen, preferably chlorine or fluorine, unsubstituted or substituted $C_1$–$C_6$ alkoxy, preferably methoxy or ethoxy, —$COOR_1$, wherein $R_1$ is hydrogen or $C_1$–$C6$ alkyl; substituted $C_1$–$C_6$ alkyl or $C_1$–$C_6$ alkoxy groups being substituted by one or more customary substituents, such as halogen, nitro, —OH, or —$COOR_1$; which process comprises: (a) preparing a dialkyl succinylsuccinate di(alkali metal) salt by reacting a mixture consisting essentially of an alkali metal alcoholate, an aliphatic alcohol and an excess of a liquid diallyl succinate under anhydrous conditions at an elevated temperature; (b) removing the aliphatic alcohol from the reaction mixture; (c) separating the solid dialkyl succinylsuccinate di(alkali metal) salt from an anhydrous supernatant liquid; (d) neutralizing the dialkyl succinylsuccinate di(alkali metal) salt to yield the dialkyl succinylsuccinate and (e) converting the dialkyl succinylsuccinate to the quinacridone.

Preferably, the quinacridone is selected from the group consisting of quinacridone, 2,9-dichloroquinacridone, 2,9-dimethylquinacridone, and 4,11-dichloroquinacridone.

Steps (a)–(d) are described above. Step (e) is carried out by processes that are well-known in the art. For example, the dialkyl succinylsuccinate is converted to a quinacridone by (aa) condensation with an aniline in the presence of an acid catalyst in a solvent to give a dialkyl 2,5-dianilino-3,6-dihydroterephthalate, which may be isolated or reacted directly; (bb) adding the product from (aa) to a high-boiling liquid (boiling point at least 250° C.) at its boiling point with removal of alcohol to yield a dihydroquinacridone; and (cc) oxidizing the dihydroquinacridone product from step (bb) with a suitable oxidant in an alkaline medium to yield the quinacridone.

The substitution of the aniline used in step (aa) controls the substitution of the final quinacridone product, for example, para-chloroaniline yields 2,9-dichloroquinacridone and para-toluidine yields 2,9-dimethylquinacridone.

The following examples describe embodiments of the invention, but do not limit the invention. All parts are parts by weight unless otherwise specified.

EXAMPLE 1

A 30% solution of sodium methylate (55.0 g., 1.02 mole) in dry methanol (126.5 g., 3.95 mole) at 30° C. under nitrogen is added over two hours via a peristaltic pump to stirred dimethyl succinate (493.9 g., 3.38 mole) at 105° C. (±5° C.) at a pressure of from 350 to 400 mm Hg. The methanol is distilled off through a short column into a graduated receiver. Upon completion of the addition, the vacuum is replaced by nitrogen at atmospheric pressure, the condenser switched to reflux and the elevated temperature is maintained for one hour. The residual methanol is subsequently distilled for an extra one hour period to remove the last traces of methanol. The resulting slurry is cooled to less than 50° C. then pumped into stirred dry methanol (320 g., 10.0 mole) and maintained at less than 30° C. After checking by microscope that all the complex has converted to the crystalline form of dimethyl succinylsuccinate disodium salt, the mixture is filtered using an inerted Buchner funnel. The filtercake is washed with anhydrous methanol, if necessary reslurrying it in anhydrous methanol followed by filtration. This washing step is repeated until the methanol washings contain less than 0.3% dimethyl succinate by gas chromatography. The combined filtrates are collected for fractionation in order to recover the methanol and dimethyl succinate. The methanol-wet filtercake is transferred, with stirring, to a neutralization vessel containing 15% aqueous sulfuric acid (332.7 g., 0.51 mole) at ambient temperature under nitrogen. After one hour at 30°–35° C., the dimethyl succinylsuccinate product is filtered. The presscake is subsequently washed with water at 30°–35° C., if necessary by reslurrying in water followed by filtration. This washing process is repeated until the filtrates show less than 0.5% methanol by gas chromatography, the pH is greater than 6.0 and the conductivity is within 5% of the incoming wash water. The water-wet presscake is weighed and a sample taken for solids content and analysis. The yield of 100% pure DMSS based on sodium methylate is 86%.

EXAMPLE 2

Example 1 is repeated except that the dimethyl succinate is made up of recovered dimethyl succinate from the distillation of the combined filtrates from several runs of Example 1. The yield of dimethyl succinylsuccinate based on sodium methylate is 87.5 percent of theory.

EXAMPLE 3

A 30% solution of sodium methylate (55.5 g., 98.6% purity, 1.01 mole) in dry methanol (126.5 g., 3.95 mole) at 30° C. under nitrogen is added over one hour via a peristaltic pump to stirred dimethyl succinate (385.1 g., 98.7% purity, 2.60 mole) at 105° C. at a pressure of 400 mm. Hg. The methanol is distilled off through a short column into a chilled graduated receiver. Upon completion of the addition, the vacuum is replaced by nitrogen at atmospheric pressure, the condenser switched to reflux and the elevated temperature is maintained for one hour. The residual methanol is then distilled out to give 196 g. distillate (contains 3.8% dimethyl succinate by g.c. analysis). The resulting slurry is cooled to 50° C. then pumped into stirred dry methanol (444 g., 13.9 mole) and maintained at 25°–30° C.. After checking by microscope that all the complex has converted to the crystalline form of dimethyl succinylsuccinate disodium salt, the mixture is filtered using an inerted Buchner funnel. The filtercake is washed with anhydrous methanol (475 g., 14.8 mole) until the methanol washings contain less than 0.3% dimethyl succinate by gas chromatography. The methanol-wet filtercake is reslurried in dry methanol (237 g., 7.4 mole) and transferred to stirred 15% aqueous sulfuric acid (328 g., 0.50 mole) at ambient temperature under nitrogen. After one hour at 30°–35° C., the dimethyl succinylsuccinate is filtered. The presscake is washed with water at 30°–35° C. until the filtrates show less than 0.5% methanol by gas chromatography, the pH is greater than 6.0 and the conductivity is within 5% of the incoming wash water. The water-wet presscake is dried in a vacuum oven at 50° C. to give 99.3 g. dimethyl succinylsuccinate of 99.5% purity for a yield of 86% of theory, based on sodium methylate.

EXAMPLE 4

To a stirred solution of dimethyl succinate (400.1 g., 98.7% purity, 2.7 mole) and dry methanol (13 g., 0.4 mole) at 30° C. under nitrogen is added over 1.5 hour a stirred slurry of finely divided sodium (22.1 g., 0.96 mole) in dimethyl succinate (83.4 g., 0.57 mole). The temperature rises to 45° C. maximum. The mixture is heated to 76° C. and the methanol stripped off over two hours. Additional dimethyl succinate is added (200 g., 1.38 mole) to maintain the fluidity of the reaction. On completion of methanol distillation, methanol is added (400 g., 12.5 mole) and the mixture cooled to 30° C., filtered and the excess dimethyl succinate washed out with dry methanol. The resulting filtercake is reslurried in methanol and added to 15% aqueous sulfuric acid (330 g.), cooled to 24° C. then filtered, washed with water to remove the sodium sulfate, and dried. A yield of 81% of theory dimethyl succinylsuccinate is obtained.

EXAMPLE 5

Dimethyl succinate (365 lb., 2.5 lb.mole) is charged to a 100 gallon stainless steel reactor and the vessel is inerted with nitrogen, then heated to 100°–105° C. A vacuum of 14 in. Hg is applied with a nitrogen purge and the dimethyl succinate is stripped of any residual moisture. A solution of 30% sodium methylate in methanol (180 lb., 1.0 lb.mole) is added via a peristaltic pump at a rate of about 0.75 lb./min.. Methanol (with any entrained dimethyl succinate) is distilled off and collected in a cooled receiver. The rate of addition is adjusted so as to keep the pot temperature at 105° C. On completion of addition, the mixture is allowed to reflux at atmospheric pressure under nitrogen for one hour. Vacuum is reapplied and the residual methanol is stripped off and added to the receiver. The reaction slurry is cooled to 90° C. and transferred to a second vessel containing stirred dry methanol (400 lb.) at 25° C. On completion of transfer, the residual slurry is flushed through with dry methanol (50 lb.) and the methanolic slurry agitated for one hour. The slurry of dimethyl succinylsuccinate disodium salt is fed to a centrifuge and the mother liquors removed. The cake is washed with dry methanol until the washings contain less than 0.3% dimethyl succinate. Nitrogen is heated and used to dry the cake on the centrifuge prior to transferring the dry powder to a collecting bag. The dry dimethyl succinylsuccinate disodium salt is then added to a stirred solution of 15% aqueous sulfuric acid (555 lb.) at 25° C. The product is filtered by centrifugation and washed with water until the filtrates show a pH >6.0 and the conductivity is within 5% of the incoming water. It is advantageous to use deionized water in the final stages. The product is dried in a vacuum paddle drier. The yield is 85% of theory. The excess dimethyl succinate and dry methanol are recovered from the combined overheads and filtrates by fractional distillation through a packed column. Both are suitable for re-use in the reaction without further purification. The residues from the distillation are dissolved in water and sent to waste neutralization.

EXAMPLE 6

Dimethyl succinylsuccinate from Example 5 (22.8 g., 0.1 mole) is dissolved in THERMINOL VP-1 (a mixture of diphenyl ether and biphenyl from Monsanto, 129.2 g.) at 90° C. under nitrogen and added over one hour to a stirred mixture of aniline (23.25 g., 0.25 mole), THERMINOL VP-1 (85 g.) and trifluoroacetic acid (0.5 g.) at 90° C. and 100 mm. Hg pressure. The water of condensation is removed and, on completion of condensation, the pressure is dropped to 15 mm. Hg and excess aniline, the trifluoroacetic acid and a part of the THERMINOL VP-1 is distilled out, replacing the distillate volume with an equal volume of fresh THERMINOL VP-1 until the distillate shows less than 0.1% aniline. The product, dimethyl 2,5-dianilino-3,6-dihydroterephthalate, is diluted to a 10% slurry with THERMINOL VP-1 and heated to solution at 160°–170° C. This solution is added over three hours to rapidly stirred, vigorously boiling THERMINOL VP-1 under nitrogen. Methanol, with entrained THERMINOL VP-1, is collected by distillation. On completion of addition, the boiling is continued for one hour, the slurry cooled to 180° C. and filtered. The dihydroquinacridone is collected by filtration and washed THERMINOL VP-1 free with methanol. The yield is about 30 g. after drying. The dihydroquinacridone is slurried in methanol (120 g.) and 50% sodium hydroxide (18 g.) added with stirring, keeping the temperature below 45° C. After agitation for one hour at 45°–55° C., 96% sulfuric acid (3 g.) is added, followed by water (33 g.) and the mixture heated to reflux. After refluxing for one hour, sodium m-nitrobenzenesulfonate (17.25 g.) is added, followed by water (19.5 g.) and the refluxing continued for three hours. Sufficient water is added to attain a temperature of 60° C. and the mixture is filtered and washed with hot water until the filtrate pH is less than 8.5 and the conductivity of the filtrate is within 10% of that of the incoming water. γ-Quinacridone, an opaque, bright red pigment, is then dried and ground. The yield from dimethyl succinylsuccinate is 93% of theory.

EXAMPLE 7

In a similar manner to Example 6, with the substitution of an equimolar proportion of p-chloroaniline for aniline, 2,9-dichlorodihydroquinacridone is obtained. Oxidation of the 2,9-dichlorodihydroquinacridone (40 g.) is accomplished by adding methanol (160 g.), 45% potassium hydroxide (160 g.) and agitating for 15 minutes at 50°–60° C. Then sodium m-nitrobenzenesulfonate (23 g.) is added, followed by water (26 g.) and the mixture heated to reflux and held at reflux for three hours. Water is added to the mixture to attain a temperature of 60° C. and the slurry filtered and washed with hot water until the filtrate shows a pH of less than 8.5 and the filtrate conductivity is within 10% of that of the incoming water. The product, 2,9-dichloroquinacridone, a magenta pigment, is dried and pulverized. The yield from dimethyl succinylsuccinate is about 92% of theory.

We claim:

1. A process for the preparation of a dialkyl succinylsuccinate, which comprises: (a) preparing a dialkyl succinylsuccinate di(alkali metal) salt by reacting a mixture consisting essentially of an alkali metal alcoholate, an aliphatic alcohol and an excess of a liquid dialkyl succinate under anhydrous conditions at an elevated temperature; (b) removing the aliphatic alcohol from the reaction mixture; (c) separating the solid dialkyl succinylsuccinate di(alkali metal) salt from an anhydrous supernatant liquid; and (d) neutralizing the dialkyl succinylsuccinate di(alkali metal) salt to yield the dialkyl succinylsuccinate.

2. A process of claim 1 wherein the percent yield based on reacted dialkyl succinate is at least 85 percent by weight.

3. A process of claim 1 wherein liquid dialkyl succinate is recovered from step (c) and recycled after purification into a subsequent step (a).

4. A process of claim 1 wherein the dialkyl succinate has two $C_1$–$C_3$ alkyl groups as the dialkyl substituents.

5. A process of claim 4 wherein the dialkyl succinate is dimethyl succinate or diethyl succinate.

6. A process of claim 1 wherein the alkali metal alcoholate is a $C_1$–$C_3$ alkali metal alcoholate.

7. A process of claim 6 wherein the alkali metal alcoholate is a sodium or potassium alcoholate.

8. A process of claim 7 wherein the alkali metal alcoholate is sodium methylate or sodium ethylate.

9. A process of claim 1 wherein the aliphatic alcohol of step (a) is a $C_1$–$C_3$ aliphatic alcohol.

10. A process of claim 1 wherein the alkali metal alcoholate is prepared in situ.

11. A process of claim 4 wherein the alkyl groups of the dialkyl succinate, the alkali metal alcoholate and the aliphatic alcohol are identical.

12. A process of claim 11 wherein the dialkyl succinate is dimethyl succinate, the alkali metal alcoholate is sodium methylate and the aliphatic alcohol is methanol.

13. A process of claim 1 wherein the alkali metal alcoholate and aliphatic alcohol are combined with the dialkyl succinate as a 10 to 50 percent by weight solution of the alkali metal alcoholate in the aliphatic alcohol.

14. A process of claim 13 wherein the solution is a 25 to 35 percent by weight solution of the alkali metal alcoholate in the aliphatic alcohol.

15. A process of claim 1 wherein from 0.1 to 0.5 moles of alkali metal alcoholate are added to the reaction mixture per mole of dialkyl succinate.

16. A process of claim 15 wherein from 0.2 to 0.4 moles alkali metal alcoholate are added to the reaction mixture per mole of dialkyl succinate.

17. A process of claim 1 wherein the aliphatic alcohol is removed according to step (b) by distillation at reduced pressure.

18. A process of claim 17 wherein the aliphatic alcohol is removed concurrently with adding a 25 to 35 percent by weight solution of the alkali metal alcoholate in the aliphatic alcohol to the dialkyl succinate.

19. A process of claim 17 wherein a suspension formed according to step (b) is maintained at the elevated temperature for a period of from 45 minutes to 2 hours prior to step (c).

20. A process of claim 19 wherein the dialkyl succinylsuccinate di(alkali metal) salt is neutralized with aqueous sulfuric acid.

21. A process of claim 1 wherein the dialkyl succinylsuccinate di(alkali metal) salt is in the form of a complex with the dialkyl succinate after step (b), and the complex is converted to non-complexed dialkyl succinylsuccinate di(alkali metal) salt prior to step (c) by combining the reaction mixture with a second anhydrous aliphatic alcohol, which is the same or different from the aliphatic alcohol used according to step (a).

22. A process of claim 21 wherein the second anhydrous aliphatic alcohol is a $C_1$–$C_3$ aliphatic alcohol.

23. A process of claim 22 wherein the $C_1$–$C_3$ aliphatic alcohol is identical to the aliphatic alcohol in step (a).

24. A process of claim 1 wherein step (c) includes one or more washing steps wherein the dialkyl succinylsuccinate di(alkali metal) salt is washed with an anhydrous organic solvent.

25. A process of claim 24 wherein the anhydrous organic solvent is a $C_1$–$C_3$ aliphatic alcohol.

* * * * *